United States Patent [19]

Voorhees

[11] 4,009,282

[45] Feb. 22, 1977

[54] TREATMENT OF PROLIFERATING SKIN DISEASES WITH PROSTAGLANDINS

[75] Inventor: John J. Voorhees, Ann Arbor, Mich.

[73] Assignee: The Regents of the University of Michigan, Ann Arbor, Mich.

[22] Filed: Aug. 25, 1975

[21] Appl. No.: 607,577

Related U.S. Application Data

[63] Continuation of Ser. No. 425,099, Dec. 17, 1973, abandoned, and a continuation-in-part of Ser. No. 324,012, Jan. 16, 1973, abandoned.

[52] U.S. Cl. .............................. 424/317; 424/305
[51] Int. Cl.² ............... A61K 31/19; A61K 31/215
[58] Field of Search ........................... 424/305, 317

[56] References Cited

OTHER PUBLICATIONS

Karasek—Internat. Symp. on Psoriasis, Proceedings (1971) pp. 271–276.

Primary Examiner—Sam Rosen
Attorney, Agent, or Firm—John J. Killinger; Roman Saliwanchik

[57] ABSTRACT

Pharmaceutical compositions for treatment of proliferating skin diseases, primarily psoriasis. The compositions comprise a pharmaceutical carrier with a prostaglandin of the PGE type including $PGE_1$, $PGE_2$, $PGE_3$, the lower alkyl esters thereof and 13,14-dihydro $PGE_1$ and alkyl esters thereof as the active ingredient.

The compositions are administered to humans and animals topically and parenterally.

6 Claims, No Drawings

TREATMENT OF PROLIFERATING SKIN DISEASES WITH PROSTAGLANDINS

CROSS-REFERENCE TO RELATED APPLICATIONS

This application is a continuation-in-part of prior copending application Ser. No. 324,012, filed Jan. 16, 1973, for "Pharmaceutical Composition and Process of Treatment", and is a continuation of application Ser. No. 425,099, filed Dec. 17, 1973 both abandoned.

BRIEF DESCRIPTION OF THE INVENTION

This invention related to pharmaceutical compositions for application to the skin and to a method for the treatment of proliferating skin diseases. The compositions may be applied topically, or by injection, intralesionally, intradermally, or sub-cutaneously. The treatment can be either therapeutic or prophylactic.

DETAILED DESCRIPTION OF THE INVENTION

Proliferative skin diseases are widespread throughout the world and afflict millions of humans and their domesticated animals. This invention provides a method for treatment of such diseases and pharmaceutical compositions which are useful in alleviating them. As used hereinafter in this specification and in the claims, the expression "proliferative skin diseases" means benign and malignant proliferative skin diseases which are characterized by accelerated cell division in the epidermis, dermis or appendages thereto, associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant kertosis, acne, and seborrheic dermatitis in humans and atopic dermatitis and mange in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful in the wide spectrum of specific diseases encompassed by the expression proliferative skin diseases.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anti-cancer agents, for example, methothrexate, hydroxyurea, azaribine, cyclophosphamide; (3) physical modalities: ultraviolet light, x-irradiation, and in severe cases, surgery.

While these treatments provide, in certain cases, some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anticancer drugs, x-irradiation, or ultra violet rays.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and and the claims hereof, psoriasis is alleviated when a scale-free psoriasis lesion is noticeably decreased in thickness, or noticeably but incompletely cleared or completely cleared.

The compositions may be applied topically or by injection intradermally, intra- or peri-lesionally, or sub-cutaneously.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional anhydrous pharmaceutical forms for this purpose include ointments, lotions, pastes, jellies, sprays, aerosols, bath oils and the like. The term "ointment"embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

The percentages by W/W of the active ingredient herein utilized ranges from about 0.1 to about 15% of the pharmaceutical payments, preferably from about 0.5 to above 2% and in these preparations the aforesaid pharmaceutical course for topical application constitutes a major amount of the sum preparation.

Injection "Intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected intramuscularly, or by application to non-diseased skin.

For parenteral administration, fluid forms are prepared utilizing the active compound and a sterile vehicle, water being preferred when the composition is to be used immediately, i.e. not stored. The compound, depending on the form and concentration used, can be either suspended or dissolved in the vehicle. In preparing solutions, a water-soluble form of the compound can be dissolved in water for injection and filter sterilized before filling into a suitable vial or ampule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized before suspending in the sterile vehicle. Advantageously, a surfactant or wetting agent is included in the composition to facilitate uniform distribution.

Injectable compositions are prepared containing a prostaglandin in a concentration W/V of from about 0.1 to about 5%.

Prostaglandin E-type compounds (PGE) and their esters included in this invention are $PGE_1$, $PGE_2$, $PGE_3$, dihydro $PGE_1$ and the alkyl esters of 1 to 8 carbon atoms, inclusive. Prostaglandin E-type compounds and their esters are known in the art. See, for example, Bergstrom, S., et al. P'Col Reviews 20:1 (1968) for $PGE_1$, $PGE_2$, $PGE_3$, Anggard, E., et al., J. Biol. Chem. 239:4097 (1964), for dihydro $PGE_1$; U.S. Pat. Nos. 3,069,322 and 3,598,858 for prostaglandin esters.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy. The glucocorticoids should be employed in minor amounts or "permissive dosage." The expression permissive dosage for glucocorticoids refers to a quantity which minimally supplements the natural output of adrenal cortical glucocorticoids in a normal person and which dosage administered, alone, has no perceptible effect on proliferative skin diseases.

The following examples describe the manner and process of making and using the invention and set forth the best mode contemplated by the inventor of carrying out the invention but are not be construed as limiting.

EXAMPLE 1

The following topical compositions are useful in treating psoriasis.

| | |
|---|---|
| $PGE_1$ | 0.1 gm |
| Spermaceti | 27 gm |
| Beeswax | 27 gm |
| Carbapol 934 q.s. | 100 gm |
| CREAM | |
| $PGE_1$ | 1 gm |
| Polyethylene glycol 400 | 37.5 gm |
| 1,2,6-hexanetriol | 20 gm |
| Polyethylene glycol 4000 z.s. | 100 gm |
| CREAM | |
| $PGE_1$ | 5 gm |
| Polyethylene glycol 400 | 37 gm |
| Polyethylene glycol 400 monostearate | 26 gm |
| Polyethylene glycol 4000 q.s. | 100 gm |

-continued

| | |
|---|---|
| CREAM | |
| $PGE_1$ | 5 gm |
| Polyethylene glycol 400 | 47.5 gm |
| Cetyl alcohol | 5 gm |
| Polyethylene glycol 4000 q.s. | 100 gm |
| OINTMENT | |
| $PGE_2$ | 10 gm |
| Anhydrous lanolin | 20 gm |
| Mineral oil | 25 gm |
| White petrolatum q.s. | 100 gm |

The above ointments and creams are useful in the treatment of psoriasis by application to the affected skin areas three times a day.

EXAMPLE 2

One liter of topical lotion is prepared from the following types and amounts of ingredients:

| | |
|---|---|
| $PGE_1$ | 20 gm |
| Propylene glycol q.s. | 1 liter |

The PGE is dissolved in the propylene glycol and filtered into 5 ml polyethylene bottles.

The composition is applied topically to psoriatic lesions three times a day.

EXAMPLE 3

Parenteral Solution

A sterile aqueous solution for injection containing in 1 cc. 10 mg of $PGE_1$, is prepared from the following types and amounts of materials:

| | |
|---|---|
| $PGE_1$ | 10 gm |
| Lidocaine hydrochloride | 4 gm |
| Methylparaben | 2.5 gm |
| Propylparaben | 0.17 gm |
| Water for injection q.s. | 1000 cc |

The ingredients are dissolved in the water and the solution sterilized by filtration. The sterile solution is filled into vials and the vials sealed. The composition is to be used immediately.

EXAMPLE 4

Parenteral Solution

A sterile aqueous solution for injection containing in 1 cc 1 mg of $PGE_1$, as the Na salt is prepared from the following types and amounts of ingredients:

| | |
|---|---|
| $PGE_1$ | 1 gm |
| Sodium chloride 10 % solution q.s. | |
| Water for injection q.s. | 1000 cc |

$PGE_1$ is added to the water and sufficient sodium chloride added to form an isotonic solution and the solution sterilized by filtration. The sterile solution is used immediately and injected intradermally by high pressure injection for the treatment of psoriasis.

EXAMPLE 5

Parenteral grade $PGE_1$ is dissolved in anhydrous N,N-dimethylacetamide containing 0.4% water (determined by the Karl Fischer Method) in the proportions of 5 mg $PGE_2$ for each ml of anhydrous N,N-dimethylacetamide. The solution is then filter sterilized by passing it through a microporous (solvent-resistant) filter e.g., Millipore Solvinert 0.25 microns or Gelman Metricel Alpha-8, 0.2 microns, aseptically packaged in 1 ml quantities in sterile ampuls and kept under refrigeration at not more than 5° until needed. At that time the contents of one ampul (1 ml) are diluted into 1 liter of infusion solution and administered by high pressure injection, intradermally for the treatment of psoriasis.

EXAMPLE 6

Parenteral grade $PGE_2$ is dissolved in spectrograde N,N-dimethylacetamide (0.1% water) in a concentration of 10 mg per ml. The solution is filter sterilized as in Example 1 and packaged aseptically in 0.5 ml quantities in sterile ampuls. This solution can be stored at room temperature. It is administered in the same way and for the same purposes as in Example 5.

EXAMPLE 7

Following the proceeding of the preceding example 1 through 6 inclusive, compositions are similarly prepared substituting each of $PGE_1$-methyl ester, $PGE_2$, $PGE_2$-methyl ester, $PGE_3$, $PGE_3$-methyl ester, 13,14-dihydro $PGE_1$ and 13,14-dihydro $PGE_1$-methyl ester from the $PGE_1$ composition are prepared which are useful for the treatment of psoriasis.

EXAMPLE 8

The compositions prepared in the preceding examples 1 through 6, inclusive, can similarly be used for the treatment of atopic dermatitis, non-specific dermatitis, primary irritant contact dermatitis, allergic contact dermatitis, basal and squamous cell carcinomas of the skin, lamellar ichthyosis, epidermolytic hyperkeratosis, permalignant sun induced keratosis, non-malignant keratosis, acne, and seborrheic dermatitis in humans and atapic dermatitis and mange in domesticated animals.

I claim:

1. A process for teating proliferating skin diseases comprising the administration of an effective amount of $PGE_1$, $PGE_2$, $PGE_3$ or the alkyl ester thereof containing from 1 to 8 carbon atoms, inclusive, or 13,14-dihydro $PGE_1$ or the alkyl esters thereof containing from 1 to 8 carbon atoms inclusive, in association with a pharmaceutical carrier to a human or animal.

2. A process according to claim 1 wherein the compound is $PGE_1$ or the alkyl ester thereof containing from 1 to 8 carbon atoms inclusive and the administration is topically.

3. A process according to claim 1 wherein the compound is $PGE_2$ or the alkyl ester thereof containing from 1 to 8 carbon atoms inclusive and the administration is topically.

4. A process according to claim 1 wherein the compound is $PGE_3$ or the alkyl ester thereof containing from 1 to 8 carbon atoms inclusive and the administration is topically.

5. A process according to claim 1 wherein the compound is 13,14-dihydro-$PGE_1$ or the alkyl ester thereof containing from 1 to 8 carbon atoms inclusive and the administration is topically.

6. The process for alleviating the symptoms of psoriasis in human skin tissue which comprises applying to the area which is psoriatic a pharmaceutical composition containing an effective amount of either $PGE_1$ or $PGE_2$.

* * * * *